United States Patent [19]

Asato

[11] 4,216,149

[45] Aug. 5, 1980

[54] DL-N-(4,5,6,7-TETRAHYDRO-7-OXOBENZO[B]THIEN-4-YL)PHTHALIMIDE

[75] Inventor: Goro Asato, Titusville, N.J.

[73] Assignee: American Cyanamid Company, Stamford, Conn.

[21] Appl. No.: 936,319

[22] Filed: Aug. 23, 1978

Related U.S. Application Data

[60] Division of Ser. No. 816,429, Jul. 18, 1977, Pat. No. 4,134,899, which is a continuation of Ser. No. 628,716, Nov. 4, 1975, abandoned.

[51] Int. Cl.² .............................................. C07D 333/54
[52] U.S. Cl. ......................... 260/326 S; 260/326.5 SA
[58] Field of Search ..................... 260/326 S, 326.5 SA

[56] References Cited

U.S. PATENT DOCUMENTS

| | | | |
|---|---|---|---|
| 3,316,259 | 4/1967 | Sam | 260/326.5 SA |
| 3,389,149 | 6/1968 | Glick et al. | 260/326.16 |
| 3,944,567 | 3/1976 | Asato | 424/275 |
| 4,060,627 | 11/1977 | Asato et al. | 424/275 |

OTHER PUBLICATIONS

J. Sam et al., J. Pharm. Sci., 54, No. 5 (1965), pp. 753–756.
J. Cymerman–Craig et al., Chem. Abstracts 51:4355f (1957).

*Primary Examiner*—Donald G. Daus
*Assistant Examiner*—M. C. Eakin
*Attorney, Agent, or Firm*—Harry H. Kline

[57] ABSTRACT

This invention relates to novel derivatives of 4,5,6,7-tetrahydro-7-oxo(oxy)benzo[b]thiophen-4-amine which are useful as animal growth regulants, and a process for the preparation thereof. The above-identified compounds of this invention are also useful as intermediates for the preparation of 4,5,6,7-tetrahydro-7-oxo(oxy)-benzo[b]thien-4-ylurea compounds.

1 Claim, No Drawings

DL-N-(4,5,6,7-TETRAHYDRO-7-OXOBENZO[B]-THIEN-4-YL)PHTHALIMIDE

CROSS REFERENCE TO RELATED APPLICATION

This is a division, of application Ser. No. 816,429, filed July 18, 1977, now U.S. Pat. No. 4,134,899; which is a cont. of Ser. No. 628,716 filed Nov. 4, 1975, now abandoned.

BACKGROUND OF THE INVENTION

The 4,5,6,7-tetrahydro-7-oxo(oxy)benzo[b]thiophen-4-amine compounds are useful as intermediates in the preparation of 4,5,6,7-tetrahydro-7-oxo(oxy)benzo[b]-thien-4-ylurea compounds which possess animal growth regulating and herbicidal activity, and which are described in detail and claimed in my co-pending Application Ser. No. 532,449, filed Dec. 13, 1974, now abandoned, and Ser. No. 572,492 filed Apr. 25, 1975, now abandoned, both of which are herein incorporated by reference.

SUMMARY OF THE INVENTION

This invention relates to novel 4,5,6,7-tetrahydro-7-oxo(oxy)benzo[b]thiophen-4-amine compounds which are represented by formula (I) below:

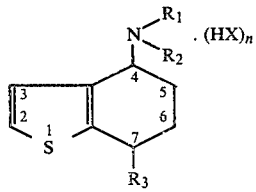

wherein $R_1$ represents hydrogen; $R_2$ is selected from the group consisting of hydrogen, $C_1-C_6$ alkanoyl, halo-substituted $C_1-C_6$ alkanoyl and

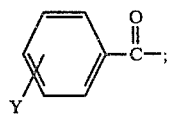

wherein Y is selected from the group consisting of hydrogen, 3,4-dichloro, chloro, methyl, methoxy and nitro; when $R_1$ and $R_2$ are taken together with the associated nitrogen they represent a moiety selected from the group of cyclic imides consisting of succinimide, maleimide, phthalimide and 1,2,3,6-tetrahydrophthalimide; $R_3$ is selected from the group consisting of oxo and hydroxyl; X is selected from the group consisting of chlorine, bromine and iodine; n is 0, except when $R_1$ and $R_2$ are both hydrogen; the racemic mixture and the optical isomers thereof, and when $R_3$ is hydroxyl the racemic mixture and optical isomers of the cis and trans isomers thereof, wherein the terms "cis" and "trans" refer to the configuration of the 7-hydroxy group with respect to the 4-amino group.

A preferred embodiment of the present invention consists of those compounds of formula (I) wherein $R_1$ is hydrogen; $R_2$ is selected from the group consisting of $C_1-C_6$ alkanoyl and halo-substituted $C_1-C_6$ alkanoyl; when $R_1$ and $R_2$ are taken together with the associated nitrogen they represent phthalimido; X is selected from the group consisting of chlorine, bromine and iodine; n is 0, except when $R_1$ and $R_2$ are both hydrogen; $R_3$ is selected from the group consisting of oxo and hydroxyl; and the racemic mixture, the cis and trans isomers thereof when $R_3$ is hydroxyl, and the optical isomers thereof.

This invention further relates to methods of preparation of the above-described formula (I), 4,5,6,7-tetrahydro-7-oxo(oxy)benzo[b]thiophen-4-amine compounds, hereinbelow described and exemplified in detail.

The novel formula (I) tetrahydro-7-oxobenzo[b]thiophen-4-amine compounds of the present invention wherein $R_3$ is carbonyl are prepared from the corresponding formula (II) 4,5,6,7-tetrahydrobenzo[b]thiophen-4-amines by an oxidation reaction which may be graphically illustrated as follows:

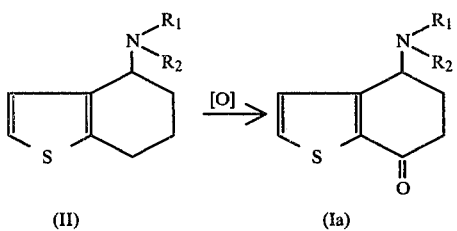

wherein $R_1$ and $R_2$ are as defined above.

A formula (II) amine is reacted with a 2 to 8 mole equivalent, preferably with a 2 to 5 mole equivalent, of an oxidizing agent selected from the group consisting of ceric ammonium nitrate, ceric sulfate, silver oxide, chromic anhydride or sodium bichromate at a temperature between about 0° C. and about 100° C., preferably 20° C., to 60° C., in a solvent selected from the group consisting of aqueous solutions of acetic acid, acetonitrile, tetrahydrofuran, dioxane, dimethoxyethane, diethylene glycol dimethyl ether, which may contain nitric acid, phosphoric acid or perchloric acid, or chromic anhydride—acetic anhyride, followed by hydrolysis. Other oxidizing agents, such as persulfates, may also be used in the above oxidation reaction if so desired.

The corresponding 7-hydroxy (cis and trans isomers, as defined above) analogs are prepared from the corresponding type (Ia) compounds, by reduction with equimolar or excess amounts of sodium borohydride, at a temperature range between about 0° C. and about 75° C., preferably 20° C. to 40° C., in $C_1-C_3$ alcohols to afford a mixture of the cis and trans isomers. The above reaction may be graphically illustrated as follows:

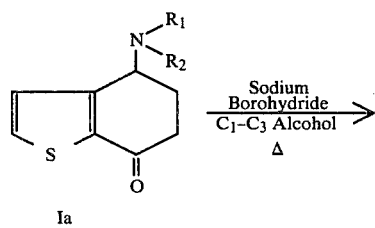

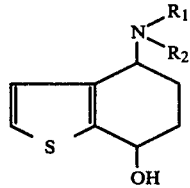

Ib (cis and trans)

wherein R₁ and R₂ are as defined above.

The 4,5,6,7-tetrahydrobenzo[b]thiophen-4-amine intermediates are represented by formula (II) below:

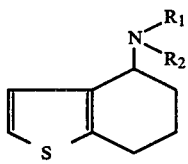
(II)

wherein $R_1$ represents hydrogen; $R_2$ is selected from the group consisting of hydrogen, $C_1$–$C_6$ alkanoyl halo-substituted $C_1$–$C_6$ alkanoyl and

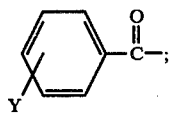

wherein Y is selected from the group consisting of hydrogen, 3,4-dichloro, chloro, methyl, methoxy and nitro; when R₁ and R₂ are taken together with the associated nitrogen they represent a moiety selected from the group of cyclic imides consisting of succinimido, maleimido, phthalimido and 1,2,3,6-tetrahydrophthalimido; and the racemic mixtures and the optical isomers thereof.

A 1 mole equivalent of 4,5,6,7-tetrahydrobenzo[b]thiophen-4-amine is reacted with a 1 to 1.5 mole equivalent of the appropriate acid anhydride or halide (preferably the acid chloride) in the presence of an anhydrous solvent, inert to the reactants, selected from aromatic hydrocarbons such as benzene, toluene and xylene; chlorinated hydrocarbons such as methylene chloride, chloroform, ethers such as tetrahydrofuran, dioxane, dimethoxyethane, diethylene glycol dimethyl ether and the like, or mixtures thereof at a temperature between about 0° C. and about 100° C., preferably 20° C. to 50° C. for a period of time from 1 hour to 24 hours. Acid acceptors such as trimethyl or triethylamine, pyridine and the like or alkali metal carbonates such as sodium or potassium carbonate may be utilized to good advantage in the above reaction when the acid halides are utilized.

The novel 4,5,6,7-tetrahydro-7-oxo(oxy)benzo[b]-thiophen-4-amine compounds of formulae Ia and Ib, obtained by the procedures hereinabove described, are racemic mixtures. Should the optically active isomers of formulae Ia and Ib compounds be desired, they may be conveniently prepared from the resolved (d or l) isomers of 4,5,6,7-tetrahydrobenzo[b]thiophen-4-amine by the above described routes.

The compounds of this invention are useful as growth promoting agents for animals such as poultry, fur-bearing and farm animals and their use for this purpose has the added advantage of improving feed conversion for said animals. The term "feed conversion" means the ratio of unit weight of feed per unit weight of gain and "improvement in feed conversion" means increased weight gain from a given unit of feed consumed.

A growth-promoting amount of a formula (I) 4,5,6,7-tetrahydro-7-oxo(oxy)benzo[b]thiophen-4-amine or an optically active isomer thereof is administered to a host animal in, or with, the animal's feed. Said compound may also be administered as a subcutaneous implant under the skin of said animal or as a parenteral injection. When administered in the feed of said animals, usually about 0.0001% to about 0.08% by weight, and preferably 0.001% to 0.04% by weight of formula (I) amine, is effective for increasing growth rate and improving feed conversion. When administered as a parenteral injection or subcutaneous implant, usually in amounts that will supply about 0.0005 mg., to about 0.2 mg., preferably 0.001 mg. to 0.10 mg. per kg. of body weight per day of the active compound, it will produce the desired improvement in weight gain and enhance food conversion.

Preparation of animal growth regulating and herbicidal urea compounds from the corresponding 4,5,6,7-tetrahydro-7-oxo(oxy)benzo[b]thiophen-4-amine compounds of the present invention may be accomplished by a number of alternate routes, as set forth in the following paragraphs.

A formula I amine, except when R₁ and R₂ are both hydrogen, is hydrolyzed in dilute mineral acid and the resulting 4,5,6,7-tetrahydro-7-oxo(oxy)benzo[b]thiophen-4-amine of formula (III) is reacted with an equimolar or excess (5% to 50%) amount of sodium or potassium cyanate at a temperature in the range of 0° C. to 100° C., preferably 0° C. to 70° C., in the presence of a solvent selected from the group consisting of water, $C_1$–$C_3$ alcohols, tetrahydrofuran, dioxane, ethylene glycol dimethyl ether, acetone, methyl ethyl ketone or the like or mixtures thereof in the pH range of 5 to 7, and preferably a pH 6. The above reaction may be graphically illustrated as follows:

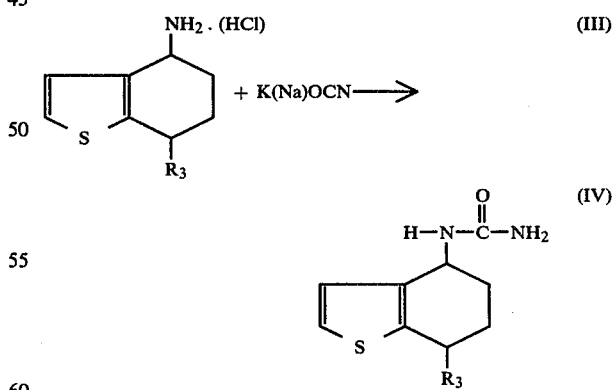

wherein $R_3$ represents oxo or hydroxy. The formula IV compounds obtained are the racemic mixtures and the cis and trans isomers thereof, wherein $R_3$ is hydroxyl.

To obtain a formula IV substituted urea of formula III amine is reacted with an isocyanate of the formula: R-NCO under conditions similar to those described above yield a formula IV urea of the structure:

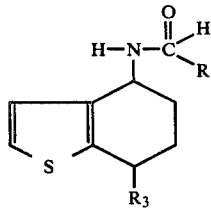

wherein $R_3$ is as defined above and R represents a substituent such as alkyl, alkoxy, benzyl, phenyl, substituted phenyl and the like selected to enhance the biological activity and/or to impart suitable physical properties to said urea.

An amine of formula (III) where $R_3$ is oxo, may be reacted with phosgene, preferably under anhydrous conditions, under a blanket of inert gas such as nitrogen. The reaction is initially carried out at a temperature between about 0° C. to about 40° C., preferably 10° C. to 20° C., and then heated to between about 50° C. and about 100° C., preferably from 60° C. to 80° C. to yield the isocyanate of formula (V):

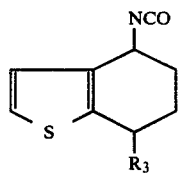

wherein $R_3$ is oxo. This reaction is usually conducted in the presence of an organic solvent such as benzene, toluene or xylene. The thus obtained isocyanate of formula (V) is then reacted with an equimolar or excess (5% to 50%) amount of an amine of the formula

to yield a formula IV urea of the structure:

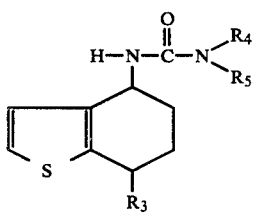

wherein $R_3$ is as defined above; $R_4$ and $R_5$ represent substituents such as alkyl, alkoxy, benzyl, aryl groups and the like selected to favorably enhance the biological activity and/or physical properties of said urea. For the preparation of compounds of formula IV, wherein $R_3$ is hydroxyl, the corresponding oxo compounds are conveniently reduced with sodium borohydride in $C_1$-$C_3$ alcohols.

The thus obtained animal growth promoting urea compounds of formula IV are the racemic mixtures of the cis and trans isomers when $R_3$ is hydroxyl; unless, of course, the reaction sequence leading to said ureas is started with the resolved (d or l) formula (III) amines.

In practice, the 4,5,6,7-tetrahydro-7-oxo(oxy)benzo[b]thien-4-ylurea compounds of formula (IV) are administered to a host animal orally or parenterally as previously described.

The present invention is further illustrated by the examples set forth below.

Specific Disclosure

EXAMPLE 1

Preparation of N-formyl-4,5,6,7-tetrahydro-7-oxobenzo[b]-thiophen-4-amine

In 725 ml of 50% aqueous acetic acid, 39 g of N-formyl-4,5,6,7-tetrahydrobenzo[b]thiophen-4-amine is stirred while 473 g of ceric ammonium nitrate is added over 15 minutes at about 25° C. After 15 minutes of additional stirring, sodium chloride is added and the mixture is extracted 3 times with dichloromethane (500, 500 and 250 ml). The combined extract is washed with brine and then with water. The water is extracted with 100 ml of dichloromethane and combined with the main dichloromethane solution. Evaporation of the dichloromethane in vacuo gives a sticky gum, which when triturated with 100 ml of ether affords 28.4 g. of the title compound, m.p. 96° C. to 106° C.

EXAMPLE 2

Preparation of N-formyl-4,5,6,7-tetrahydro-7-oxobenzo[b]-thiophen-4-amine

A suspension of 22.4 g of ceric sulfate in 50% aqueous acetic acid is stirred overnight at room temperature and 2 g of N-formyl-4,5,6,7-tetrahydrobenzo[b]thiophen-4-amine is added. After 6 hours, the mixture is filtered, and the filter cake is washed with 50% aqueous acetic acid. The work-up procedure of Example 1 is then followed with the filtrate to give 1.1 g of the title compound, m.p. 102 to 114° C.

EXAMPLE 3

Preparation of N-formyl-4,5,6,7-tetrahydro-7-oxobenzo[b]-thiophen-4-amine

In 6 ml of acetic anhydride, 1 g of N-formyl-4,5,6,7-tetrahydrobenzo[b]thiophen-4-amine is stirred and 1.52 g of chromium trioxide is 6.8 ml of acetic anhydride is added at 15° C. to 28° C. over 45 minutes. After 2 hours the mixture is poured into ice-water, and after an overnight period the aqueous mixture is saturated with sodium chloride and extracted with 2×100 ml of dichloromethane. The combined extract is washed with brine and evaporated to dryness to afford 0.84 g of a brown oil. Trituration of the oil with ether affords 0.5 g of the title compound, m.p. 109° C. to 112° C.

Oxidation of N-formyl-4,5,6,7-tetrahydrobenzo[b]thiophen-4-amine with chromic acid/acetic acid, ceric ammonium nitrate/potassium permanganate/aqueous acetic acid, potassium peroxydisulfate/silver nitrate/aqueous acetic acid, t-butyl chromate/carbon tetrachloride, chromium trioxide/pyridine/dichloromethane, sodium dichromate/acetic anhydride/acetic acid, sodium dichromate/acetic acid, chromium trioxide/aqueous acetic acid, and chromium trioxide/acetic anhydride/acetic acid, respectively, also affords the title compound.

EXAMPLE 4

Preparation of N-Acetyl-4,5,6,7-tetrahydro-7-oxobenzo[b]-thiophen-4-amine

A solution of 2.15 g of N-acetyl-4,5,6,7-tetrahydrobenzo[b]thiophen-4-amine in 12 ml of acetic acid is stirred and 3.04 g of chromium trioxide in 13.6 ml of acetic anhydride is added in 15 minutes at 10° C. to 15° C. After an hour at 20° C., 20 ml of water is added and the mixture is allowed to stand overnight. Additional water (50 ml) is added, the mixture is saturated with sodium chloride and extracted with trichloromethane (100, 150 and 50 ml volumes). The combined extract is washed with brine and then with water. The water wash is extracted with trichloromethane and the extract is combined with the main trichloromethane extract. Evaporation of the extract affords a yellow-green residue, which after trituration with ether gives 1.32 g of the title compound, m.p. 160° C. to 164° C.

EXAMPLE 5

Preparation of N-trichloroacetyl-4,5,6,7-tetrahydro-7-oxobenzo[b]thiophen-4-amine Into 2 equivalents of trichloroacetic anhydride, 1 equivalent of 4,5,6,7-tetrahydrobenzo[b]thiophen-4-amine is added to afford the amide, which is collected and dried. The N-trichloroacetyl-4,5,6,7-tetrahydrobenzo[b]thiophen-4-amine melts at 80° C. to 86° C. This material is then oxidized in the manner described in Example 1 to afford the title product, m.p. 167° C. to 171° C.

EXAMPLE 6

Preparation of N-chloroacetyl-4,5,6,7-tetrahydrobenzo[b]-thiophen-4-amine

A mixture of 7.59 g of 4,5,6,7-tetrahydrobenzo[b]thiophen-4-amine hydrochloride is stirred in 60 ml of dry tetrahydrofuran and 10.1 g of triethylamine in 20 ml of dry tetrahydrofuran is added. After stirring under a nitrogen atmosphere for 15 minutes, 3.5 ml or 5.25 g of chloroacetyl chloride in 30 ml of dry tetrahydrofuran is added dropwise, while the temperature is maintained at 30° C. to 40° C. After an hour of stirring, the mixture is filtered, the filter cake is washed with tetrahydrofuran, and the filtrate is evaporated to dryness. The residue is then triturated with water and the title compound, m.p. 115° C. to 119° C., is collected and washed with water and hexane.

EXAMPLE 7 to 27

The following compounds, exemplified by structure B, are prepared by following the method of Example 1. The corresponding starting materials, exemplified by structure A, are prepared by the methods of either Example 5 or Example 6.

| Example | R |
|---------|---|
| 7 | CCl$_3$ |
| 8 | CH$_2$Cl |
| 9 | CHCl$_2$ |
| 10 | CF$_3$ |
| 11 | CH$_2$CH$_3$ |
| 12 | CH(CH$_3$)$_2$ |
| 13 | CH$_2$—C(CH$_3$)$_3$ |
| 14 | (CH$_2$)$_4$CH$_3$ |
| 15 | —C$_6$H$_5$ |
| 16 | 4-chlorophenyl |
| 17 | 2-chlorophenyl |
| 18 | 3-chlorophenyl |
| 19 | 4-nitrophenyl |
| 20 | 3-nitrophenyl |
| 21 | 2-nitrophenyl |
| 22 | 4-methoxyphenyl |
| 23 | 2-methoxylphenyl |
| 24 | 4-methoxylphenyl |
| 25 | 2-methylphenyl |
| 26 | 3-methylphenyl |
| 27 | 4-methylphenyl |
| 28 | 3,4-dichlorophenyl |

EXAMPLE 29

Preparation of N-(4,5,6,7-tetrahydro-7-oxobenzo[b]thien-4-yl)-phthalimide

In 50 ml of toluene, 5 g of 4,5,6,7-tetrahydrobenzo[b]thiophen-4-ylamine, 4.84 g of phthalic anhydride, and 0.5 ml of triethylamine are heated at reflux to azeotropically remove water. After the distillation of water is completed, the mixture is cooled, the crystals are collected and washed with ether to afford N-(4,5,6,7-tetrahydrobenzo[b]thien-4-yl)phthalimide, m.p. 166° C. to 167.5° C. Oxidation of this compound by the method of Example 1 affords the title compound, m.p. 163° C. to 166° C.

Acid hydrolysis hydrochloric acid/ethanol of this imide affords 4,5,6,7-tetrahydro-7-oxobenzo[b]thiophen-4-amine hydrochloride.

Similarly, use of maleic anhydride, cis-1,2,3,6-tetrahydrophthalic anhydride, and succinic anhydride in place of phthalic anhydride affords N-(4,5,6,7-tetrahydro-7-oxobenzo[b]thien-4-yl)maleimide, -cis-1,2,3,6-tetrahydrophthalimide and -succinimide, respectively.

EXAMPLE 30

Preparation of 4,5,6,7-tetrahydro-7-oxobenzo[b]thiophen-4-amine and its hydrochloride salt A 2 g sample of N-formyl-4,5,6,7-tetrahydro-7-oxobenzo[b]thiophen-4-amine is heated at reflux with 10 ml of 95% ethanol and 10 ml of 2 N hydrochloric acid for 5 hours. The solution is evaporated to dryness and the residue triturated with acetone to afford the title compound, m.p. 224° C. to 225° C. dec. Substitution of hydrochloric acid with hydrobromic acid or hydroiodic acid affords the corresponding salts of the amine. Neutralization of the hydrochloride salt with 10% aqueous sodium hydroxide and extracting the aqueous mixture with ethylene dichloride, followed by evaporation of ethylene dichloride affords 7-oxobenzo[b]thiophen-4-amine.

In the same manner, acid hydrolyses of compounds of structure B (Examples 4 to 28) also afford the above title amine hydrochloride while alkaline hydrolyses (1 equivalent of potassium hydroxide/ethanol in nitrogen atmosphere) of the same ketoamides afford the title amine.

EXAMPLE 31

Preparation of 4,5,6,7-tetrahydro-7-oxobenzo[b]thien-4-ylurea

An aqueous solution of 4,5,6,7-tetrahydro-7-oxobenzo[b]thiophen-4-amine hydrochloride (1.01 g/5 ml water) is treated with 0.81 g of potassium cyanate in 2 ml of water at pH 6–7 to afford the title compound, which is collected and washed with water to afford 0.93 g, m.p. 241° C. to 242° C. dec.

EXAMPLE 32

1-Methyl-3-(4,5,6,7-tetrahydro-7-oxobenzo[b]thien-4-yl)urea

In 50 ml of dichloromethane, 8.1 g of 4,5,6,7-tetrahydro-7-oxobenzo[b]thiophen-4-amine is stirred under a nitrogen atmosphere and 2.9 g of methyl cyanate in 50 ml of dichloromethane is added dropwise at below 30° C. After stirring for an hour, the title compound is collected, m.p. 212° C. to 215° C.

EXAMPLE 33

Preparation of (-) N-formyl-4,5,6,7-tetrahydrobenzo[b]thiophen-4-amine

In 275 ml of toluene, 52.45 g of (+) 4,5,6,7-tetrahydrobenzo[b]thiophen-4-amine is stirred under a nitrogen atmosphere and 40 ml of 97% formic acid is added in 15 minutes at about 35° C. The mixture is then heated to reflux and water is removed by azeotroping. After water no longer is distilled over, the mixture is cooled and the white titel compound is collected and washed with toluene. The title compound melts at 132.5° C. to 134° C., with $[\alpha]_D^{24} = -119.7°$ C., C=4.01 in acetic acid.

Similarly (-) N-acetyl-4,5,6,7-tetrahydrobenzo[b]thiophen-4-amine is prepared by using acetic anhydride instead of formic acid.

EXAMPLE 34

Preparation (-) N-formyl-4,5,6,7-tetrahydro-7-oxobenzo[b]thiophen-4-amine

The ceric ammonium nitrate oxidation of (-) N-formyl-4,5,6,7-tetrahydrobenzo[b]thiophen-4-amine by the method of Example 1 affords the title compound, m.p. 130° C. to 136° C., $[\alpha]_D^{24} = -144.4°$ C., C=0.514 in acetic acid.

Similarly, (-) N-acetyl-4,5,6,7-tetrahydrobenzo[b]thiophen-4-amine is oxidized to afford (-) N-acetyl-4,5,6,7-tetrahydro-7-oxobenzo[b]thiophen-4-amine.

EXAMPLE 35

Preparation of (-) 4,5,6,7-Tetrahydro-7-oxobenzo[b]thien-4-ylurea

An appropriate amount of (-) N-formyl-4,5,6,7-tetrahydro-7-oxobenzo[b]-thiophen-4-amine is hydrolyzed by the method of Example 30 and coverted to the title compound by the method of Example 31. The product melts at 247° C. to 249.5° C. dec, with $[\alpha]_D^{24} = -97.2°$ C., C=0.141 in methanol.

EXAMPLE 36

Preparation of 4,5,6,7-Tetrahydro-7-hydroxy-benzo[b]thien-4-ylacetamide

Twenty-seven g (0.129 M) of 4,5,6,7-Tetrahydro-7-oxobenzo[b]thien-4-ylacetamide is dissolved in absolute ethanol (270 ml) and treated with sodium borohydride (4.9 g, 0.129 M). The mixture is stirred at room temperature overnight, water (250 ml) is added and stirring continued for 2 hours. The bulk of the ethanol is evaporated and the precipitated solid is filtered off, washed twice with water (total 50 ml) and air dried to afford the title compound (13.73 g, 50.4% yield) as an off white solid, m.p. 175° C. to 179° C. dec.

The analytical specimen is obtained by recrystallization from acetone/hexane and melts at 170° C. to 178° C. dec. The mother liquors on standing furnish a second crop of title compound (10.83 g, 39.7% yield), m.p. 102° C. to 145° C. dec.

EXAMPLE 37

Mouse Growth Regulant Tests

CFI female mice from Carworth Farm are received when they are 6 weeks olds. They are housed 10 to a cage in air-conditioned rooms (72° F. to 76° F.) with automatically controlled lights, 14 hours on and 10 hours off. The basal diet used in these studies is Purina Laboratory Chow (see description below), which is supplied ad libtium. Water is also allowed ad libitum.

Thirteen days after arrival, the mice are weighed in groups of 10 and assigned at random to the different treatments. The concentration of the different compounds in the diet is indicated in the following Table. Twelve days later the mice are weighed again and the experiment terminated. At least 3 cages (30 mice) of untreated controls are included in each test. Test data are provided in Table I below wherein data are reported as percent weight gain over controls. The following is a description of the diet to which the growth promoting compounds are added.

| Diet | |
|---|---|
| Guaranteed Analysis | |
| Crude protein not less than | 23.0% |
| Crude fat not less than | 4.5% |
| Crude fiber not more than | 6.0% |
| Ash not more than | 9.0% |
| Ingredients | |
| Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide. | |

Effectiveness of 4,5,6,7-Tetrahydro-7-oxo(oxy)benzo[b]thiophen-4-amines As Animal Growth Promoting Agents Reported as Percent Weight Over Controls Using Mice as the Test Animal

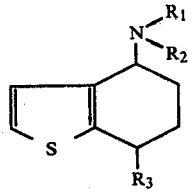

| Rate ppm in Diet | $R_1$ | $R_2$ | $R_3$ | % Weight Gain Over Controls |
|---|---|---|---|---|
| 400 | H | $CH_3CO$ | oxo | 38.5 |
| 400 | H | $CH_3CO$ | hydroxyl | 18.5 |
| 400 | 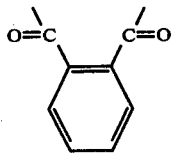 | | oxo | 9.5 |

EXAMPLE 38

By the method of Example 37, the animal growth promoting activity of tetrahydro-7-oxobenzo[b]thien-4-ylureas derived from the compounds of the present invention is evaluated. The data obtained is provided in Table II.

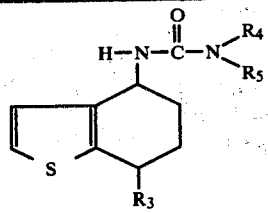

| Rate ppm in Diet | $R_4$ | $R_5$ | $R_3$ | % Weight Gain Over Control |
|---|---|---|---|---|
| 400 | H | H | oxo | 134 |
| 25 | H (levorotary) | H | oxo | 135 |

EXAMPLE 39

Preparation of 4,5,6,7-Tetrahydro-7-oxobenzo[b]thien-4-ylurea

A sample of 18.95 g of N-acetyl-4,5,6,7-tetrahydro-7-oxobenzo[b]thiophen-4-amine is heated to reflux temperature with 6N hydrochloric acid for 4 hours. The mixture is cooled, filtered through glass wool to remove tars and the tars are washed twice with 75 ml of water. The combined washes and filtrate is washed with dichloromethane and then evaporated to dryness in vacuo. The residue is dissolved in 75 ml of water and a solution of 12.5 g of potassium cyanate in 35 ml of water is added rapidly. After stirring overnight, the product is collected by filtration and washed with water and then with methanol. This affords 7.7 g of the title compound, m.p. 231° C. to 234° C. dec.

I claim:
1. The compund dl-N-(4,5,6,7-tetrahydro-7-oxobenzo[b]thien-4-yl)phthalimide.